United States Patent
Marar et al.

(10) Patent No.: US 7,575,375 B2
(45) Date of Patent: Aug. 18, 2009

(54) SYSTEMS AND METHODS FOR REDUCING MOVEMENT OF AN OBJECT

(75) Inventors: Rajeev Ramankutty Marar, Waukesha, WI (US); Ashes Dhanna Ganguly, Wauwatosa, WI (US)

(73) Assignee: General Electric Company, Schenectady, NY (US)

(*) Notice: Subject to any disclaimer, the term of this patent is extended or adjusted under 35 U.S.C. 154(b) by 181 days.

(21) Appl. No.: 11/652,358

(22) Filed: Jan. 11, 2007

(65) Prior Publication Data

US 2008/0170665 A1 Jul. 17, 2008

(51) Int. Cl.
*A61B 6/08* (2006.01)
(52) U.S. Cl. ........................................ 378/205
(58) Field of Classification Search .................. 378/19, 378/205, 206, 9, 62, 98.8, 98.11, 98.12; 250/370.08, 250/370.09
See application file for complete search history.

(56) References Cited

U.S. PATENT DOCUMENTS

| | | |
|---|---|---|
| 4,628,793 A | 12/1986 | Roth |
| 4,649,277 A | 3/1987 | Terra et al. |
| 5,514,873 A | 5/1996 | Schulze-Ganzlin et al. |
| 6,256,372 B1 | 7/2001 | Aufrichtig et al. |
| 6,282,264 B1 | 8/2001 | Smith et al. |
| 6,838,672 B2 | 1/2005 | Wagenaar et al. |
| 6,882,700 B2 | 4/2005 | Wang et al. |
| 6,901,159 B2 | 5/2005 | Baertsch et al. |
| 6,928,145 B2 | 8/2005 | Kobayashi |
| 6,935,779 B2 | 8/2005 | Zhang et al. |
| 7,009,638 B2 | 3/2006 | Gruber et al. |
| 7,054,409 B2 * | 5/2006 | Ross et al. ................ 378/19 |
| 2004/0125917 A1 | 7/2004 | Ross et al. |

* cited by examiner

*Primary Examiner*—Courtney Thomas
(74) *Attorney, Agent, or Firm*—Armstrong Teasdale LLP

(57) ABSTRACT

A system for reducing movement of an object is described. The system includes a first detector configured to detect a first beam and a second detector configured to detect a second beam. The first and second detectors are located within a radiography room.

20 Claims, 13 Drawing Sheets

SYSTEMS AND METHODS FOR REDUCING MOVEMENT OF AN OBJECT

BACKGROUND OF THE INVENTION

This invention relates generally to medical imaging systems and more particularly to systems and methods for reducing movement of an object.

X-ray systems, such as digital radiographic imaging systems, include an x-ray tube and a detector. The x-ray tube is moveably mounted to a mounting structure such as a wall or ceiling in an examination room, and the detector is provided on a horizontal table or vertical stand.

In a typical setup, the x-ray tube is mounted to a rail provided on the ceiling of the examination room, and the detector is provided on a stand positioned against a wall of the examination room. The x-ray tube is moveable in longitudinal, latitudinal, and vertical directions, and may also be rotationally moved to a number of angular positions. The detector can also be moveable, typically in a latitudinal and vertical direction. Due to the large variety of possible positions, the x-ray systems are calibrated such that the x-ray tube is directed at a lateral and vertical center of the detector at a known source to image distance (SID). However, calibrating the x-ray systems for multiple times can be tedious, time consuming, and costly.

BRIEF DESCRIPTION OF THE INVENTION

In one aspect, a system for reducing movement of an object is described. The system includes a first detector configured to detect a first beam and a second detector configured to detect a second beam The first and second detectors are located within a radiography room.

In another aspect, a system for reducing movement of an object is described. The system includes a source configured to generate a first beam and a second beam. The system further includes a detector configured to detect the first beam at a first position of the detector. The detector is configured to detect the second beam at a second position of the detector and the first position is other than the second position.

In yet another aspect, an imaging system is described. The imaging system includes a first detector configured to detect a first beam and a second detector configured to detect a second beam. The first and second detectors are located within a radiography room. The imaging system further includes an image processor configured to generate at least one image from image data acquired from at least one of a portion of the first beam and a portion of the second beam.

DETAILED DESCRIPTION OF THE INVENTION

Figure 1:
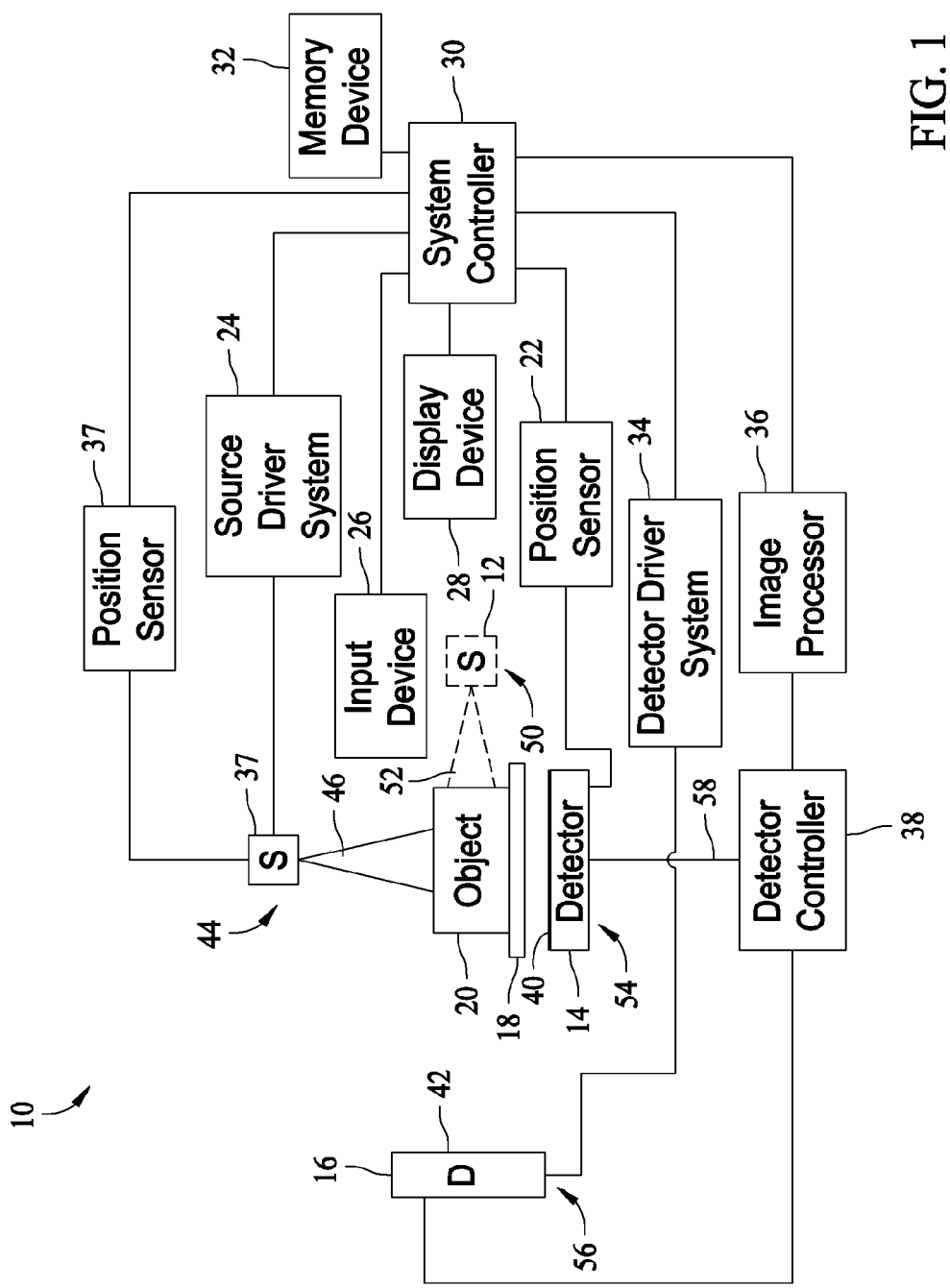
FIG. 1 is a block diagram of an embodiment of a system for reducing movement of an object of a subject.

FIG. 1 is a block diagram of an embodiment of a system 10 for reducing movement of an object. System 10 includes a source 12, a detector 14, a detector (D) 16, and a support 18, such as a table, that supports an object 20 of a subject, such as a person or a phantom. System 10 further includes a detector position sensor 22, a source driver system 24, an input device 26, a display device 28, a system controller 30, a memory device 32, a detector driver system 34, an image processor 36, a source position sensor 37, and a detector controller 38. Examples of source 12 include an x-ray source and a gamma ray source. As used herein, the term controller is not limited to just those integrated circuits referred to in the art as a controller, but broadly refers to a processor, a computer, a microcontroller, a microcomputer, a programmable logic controller, an application specific integrated circuit, and any other programmable circuit. The computer may include a device, such as, a floppy disk drive or compact disc-read-only memory (CD-ROM) drive, for reading data from a computer-readable medium, such as a floppy disk, a CD-ROM, a magneto-optical disk (MOD), or a digital versatile disc (DVD). In another embodiment, system controller 30 executes instructions stored in firmware. Moreover as used herein, the term processor is not limited to just those integrated circuits referred to in the art as a processor, but broadly refers to a controller, a microcontroller, a microcomputer, a programmable logic controller, an application specific integrated circuit, and any other programmable circuit.

Each detector 14 and 16 is a solid state digital detector. Examples of input device 26 include a keyboard and a mouse. Examples of display device 28 include a cathode ray tube (CRT) and a liquid crystal display (LCD). Memory device 32 can be a volatile memory or alternatively a non-volatile memory. Examples of memory device 32 include a ROM and a random access memory (RAM). Memory device 32 may be a computer-readable medium, such as a hard disc, a CD-ROM, an MOD, or a DVD.

A user or a person enters, via input device 26, a plurality of acquisition parameters that are stored within memory device 32. An example of the acquisition parameters includes a perpendicular distance, parallel to or along a y-axis, between a focus of source 12 and detector 14 when detector 14 is used to scan object 20 to generate a plurality of electrical signals. Another example of the acquisition parameters includes a perpendicular distance, parallel to a z-axis between a focus of source 12 and detector 16 when detector 16 is used to scan object 20 to generate a plurality of electrical signals. Yet other examples of the acquisition parameters include an angle formed between a plane 40 of detector 14 and a plane 42 of detector 16 and a distance, parallel to the z-axis, between detector 14 and detector 16. Further examples of the acquisition parameters include a field-of-view, on each detector 14 and 16, from which data is read by detector controller 38. Yet other examples of the acquisition parameters include a position of source 12 and detector 14 to obtain an image of a top view, such as either a posterior side or an anterior side, of object 20 and a position of source 12 and detector 16 to obtain a side view, such as a view of a lateral side, of object 20. Yet other examples of the acquisition parameters include a type, such as a spine, a heart, or a limb, of object 20. Still other acquisition parameters include a period of time during which source 12 is activated or energized.

Based on the acquisition parameters, system controller 30 sends a system controller command signal to source driver system 24. Source driver system 24 drives source 12 to a position 44 at a specific perpendicular distance from detector 14 based on system the controller command signal. Source position sensor 37, such as an optical encoder or a potentiometer, senses a position, such as position 44, of source 12 with respect to detector 14 and provides the position 44 to system controller 30. Upon receiving the position, such as position 44, sensed by source position sensor 37, system controller 30 controls source driver system 24 to bring source 12 to a specific position, such as a distance parallel to the y-axis between source 12 and detector 14, specified, within the acquisition parameters, by the user via input device 26. Moreover, based on the system controller command signal, a power supply within source driver system 24 provides an amount of power to source 12 to activate or turn on source 12 for a specific period of time, when source 12 is at position 44.

Upon activation at position 44, source 12 generates a beam 46, such as an x-ray beam or a gamma ray beam. Beam 46 impacts on a top portion, such as a posterior side or an anterior side, of object 20 and a portion of beam 46 is detected by detector 14. Detector 14 converts a plurality of high energy photons such as x-ray or gamma ray photons, within the portion detected by detector 14 to a plurality of low energy photons and subsequently to a plurality of electrical signals, which are processed, by image processor 36 to generate an image, such as an x-ray image or a gamma ray image, of the top portion of object 20. The low energy photons have energies lower than the high energy photons. For example, image processor 36 reconstructs the x-ray image by applying filtered backprojection (FBP) or alternatively maximum intensity projection (MIP) to image data acquired by detector controller 38. Detector controller 38 reads the electrical signals from detector 14 to acquire image data or a view of object 20 when source 12 is at position 44. System controller 30 stores the image within memory device 32 and the image may be displayed on display device 28.

It is noted that system 10 may be located in a room, such as a radiography room or an emergency room. As an example, the emergency room is the radiography room. As another example, the emergency room is an emergency room of a medical facility, such as a hospital. In another embodiment, system 10 except for system controller 30, memory device 32, input device 26, image processor 36 and display device 28 are located in the room.

Based on the acquisition parameters, system controller 30 sends a system controller command signal to source driver system 24. Upon receiving the system controller command signal, source driver system 24 drives source 12 from position 44 to a position 50 at a certain perpendicular distance, measured parallel to the z-axis, from detector 16. Source position sensor 37 senses a position, such as position 50, of source 12 to provide to provide the position to system controller 30. Upon receiving the position, such as position 50, sensed by source position sensor 37, system controller 30 controls source driver system 24 to drive source 12 to bring source 12 to a certain position, which is at a distance parallel to the z-axis between source 12 and detector 16, specified, within the acquisition parameters, by the user via input device 26. Moreover, based on system controller command signal, the power supply, within source driver system 24, provides an amount of power to source 12 to activate source 12 for a certain period of time when source 12 is at position 50.

Upon activation at position 50, source 12 generates a beam 52, such as a gamma ray beam or an x-ray beam. Beam 52 is incident on a side portion, such as a lateral side, of object 20 to generate a portion of beam 52. Detector 16 receives the portion of beam 52 when source 12 is at position 50. If the top portion is a posterior or alternatively an anterior side of object 20, the side portion is a lateral side of object 20 and if the top portion is a lateral side of object 20, the side portion is an anterior side or alternatively a posterior side of object 20.

Detector 16 converts a plurality of high energy photons, such as gamma ray or x-ray photons, within the portion of beam 52 detected by detector 16 to a plurality of low energy photons and subsequently to a plurality of electrical signals that are read by detector controller 38 and processed by image processor 36 to generate an image, such as an x-ray image or a gamma ray image, of the side portion of object 20. Detector controller 38 reads the electrical signals from detector 16 to acquire image data or a view of object 20 when source 12 is at position 50. System controller 30 stores, within memory device 32, the image acquired when source 12 is at position 50 and the image may be displayed on display device 28.

It is noted that the acquisitions parameters are input by the user via input device 26 to system controller 30 before source 12 moves from position 44 to position 50 or alternatively from position 50 to position 44. For example, system controller 30 does not receive the acquisition parameters from the user between an end of acquisition of the image data from detector 14 when source 12 is at position 44 and detector 14 at position 54 and a beginning of the acquisition of the image data from detector 16 when source 12 is at position 50 and detector 16 at position 56.

In an embodiment, image processor 36 combines, such as sums, image data acquired when source 12 is at position 44 with image data acquired when source 12 is at position 50 to generate combined image data and processes the combined image data to generate a three-dimensional (3D) image of object 20. For example, image processor 36 applies FBP or alternatively MIP to the combined image data to generate the 3D image.

In another embodiment, system 10 does not include detector 14. In yet another embodiment, image data is acquired from detectors 14 and 16 when an angle formed between plane 40 of detector 14 and plane 42 of detector 16 ranges from and including one degree to 120 degrees. It is noted that in still another embodiment, based on the acquisition parameters, source 12 moves from position 50 to position 44 instead of from position 44 to position 50 to acquire image data of object 20.

In another embodiment, system 10 does not include detector 16 and based on the acquisition parameters, system controller 30 sends a system controller command signal to detector driver system 34. Upon receiving system controller command signal from system controller 30, detector driver system 34 drives detector 14 to a position 54 when source 12 is at position 44. When source 12 is at position 44 and detector 14 is at position 54, beam 46 is generated and detector 14 detects the portion of beam 46. Detector position sensor 22 senses position 54 of detector 14 and provides the position 54 to system controller 30. System controller 30 receives the position 54 from detector position sensor 22 and controls detector driver system 34 to drive detector 14 to a specific position, which is at a perpendicular distance parallel to the y-axis between source 12 and detector 14, specified, within the acquisition parameters. Image processor 36 generates an image from the image data acquired from the portion of beam 46 detected by detector 14 at position 54.

Upon acquisition of the image data when detector 14 is at position 54 and source 12 is at position 44, system controller 30 sends a system controller command signal to detector driver system 34. Upon receiving system controller command signal from system controller 30, detector driver system 34 drives detector 14 to a position 56 from position 54. Moreover, when detector 14 is at position 56, system controller 30 also sends a system controller command signal to source 12 to drive source 12 from position 44 to position 50. Detector position sensor 22 senses position 56 of detector 14 and provides the position 56 to system controller 30. System controller 30 receives the position 56 sensed by detector position sensor 22 and controls detector driver system 34 to drive detector 14 to a specific position, which is at a perpendicular distance parallel to the z-axis between source 12 and detector 14, specified by the acquisition parameters. When source 12 is at position 50 and detector 14 is at position 56, beam 52 is generated and detector 14 detects the portion of beam 52 to generate a plurality of electrical signals. When source 12 is at position 50 and detector 14 is at position 56, detector controller 38 acquires image data from detector 14 by reading the image data from detector 14. Image processor 36 generates an image, such as an x-ray image or a gamma ray image, from the image data acquired from the portion detected by detector 14 at position 56 when source 12 is at position 50.

System controller 30 receives the acquisition parameters from the user before source 12 moves from position 44 to position 50 and detector 14 moves from position 54 to position 56. For example, the user does not provide the acquisition parameters, via input device 26, to system controller 30 between an end of the acquisition of image data when source 12 is at position 44 and detector 14 is at position 54 and a beginning of the acquisition of image data when source 12 is at position 50 and detector 14 is at position 56.

In one embodiment, system controller 30 does not receive the acquisition parameters from the user before source 12 moves from position 50 to position 44 and detector 14 moves from position 56 to position 54. For example, the user does not provide the acquisition parameters via input device 26 to system controller 30 between an end of the acquisition of image data when source 12 is at position 50 and detector 14 is at position 56 and a beginning of the acquisition of image data when source 12 is at position 44 and detector 14 is at position 54.

Moreover, in another embodiment, image processor 36 combines the image data acquired when source 12 is position 44 and detector 14 is position 54 with the image data acquired when source 12 is at position 50 and detector 14 is at position 56 to generate combined image data and generates a 3D image from the combined image data. For example, image processor 36 adds the image data acquired when source 12 is at position 44 and detector 14 is at position 54 with the image data acquired when source 12 is at position 50 and detector 14 is at position 56 to generate added image data and reconstructs, such as by applying FBP or MIP, a 3D image from the added image data. It is noted that in yet another embodiment, based on the acquisition parameters, source 12 moves from position 50 to position 44 instead of from position 44 to position 50 and detector 14 moves from position 56 to position 54 instead of from position 54 to position 56 to acquire image data of object 20.

In another embodiment, detector controller 38 is located within detector 14. In yet another embodiment, a link 58 between detector controller 38 and detector 14 is a wired or tethered link. In yet another embodiment, detector 14 is electrically coupled to detector controller 38 via a detector power supply that supplies power to detector 14 via a wired connection between the detector power supply and detector 14. In still another embodiment, detector 14 and detector controller 38 are electrically connected to each other via a wireless connection.

Figure 2:
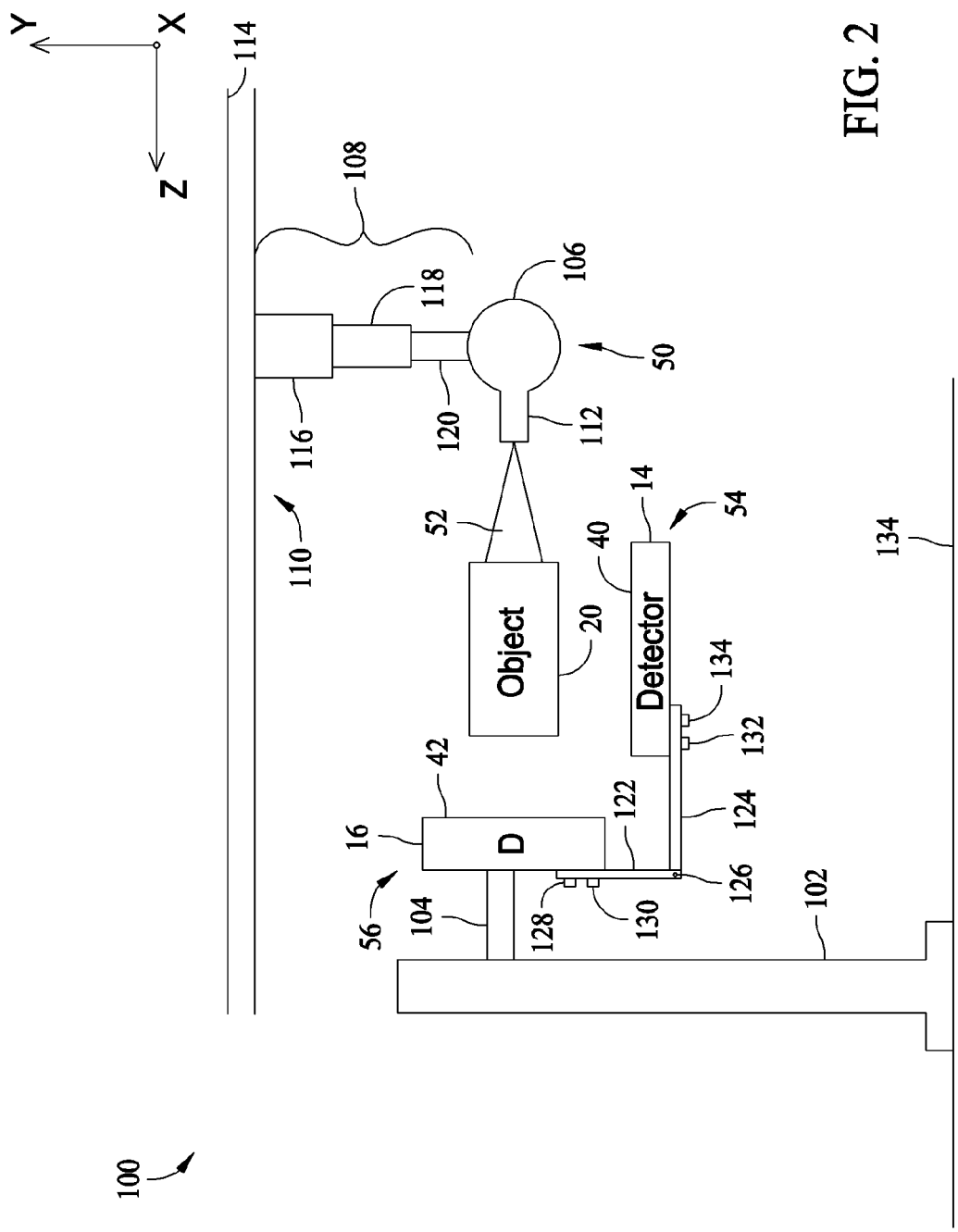
FIG. 2 is a side view of an embodiment of a system for reducing movement of an object.

FIG. 2 is a side view of an embodiment of a system 100 for reducing movement of an object. System includes a detector stand 102, a detector holder 104, detectors 14 and 16, and a source 106 supported by a telescopic column 108, and a track system 110. An example of detector stand 102 includes a wall-stand. Source 106 includes a nozzle 112. Track system 110 is attached to, such as glued with or bolted to, a ceiling 114 of the room. Source 106 is an example of source 12 and a combination of track system 110 and telescopic column 108 is an example of source driver system 24. Telescopic column 108 includes a plurality of portions 116, 118, and 120. The user mechanically couples detector 14 to detector 16 via a plurality of supports 122 and 124, such as metal bars or metal plates. The user also provides a hinge 126 between support 122 and support 124. The user mechanically couples support 122 with detector 16 via an attachment mechanism, such as a plurality of screws 128 and 130 or glue. Similarly, the user mechanically couples support 124 with detector 16 via an attachment mechanism, such as a plurality of screws 132 and 134 or glue. An angle formed support 122 and support 124 ranges from and including one degree to 180 degrees. For example, the user changes a position of support 122 with respect to support 124 to form an angle of 90 degrees between planes 40 and 42.

Detector 16 is supported by detector holder 104 that is mechanically attached to detector stand 102 located on a floor 134 of the room. System 100 is located within the room. Based on the acquisition parameters, system controller 30 controls source 106 via source driver system 24 to position source 106 at position 50. When source 106 is at position 50, an output of nozzle 112 from which beam 52 is output faces plane 42 of detector 16. When source 106 is at position 50, beam 52 is generated and an image of object 20 is generated by image processor 36 from the electrical signals generated by detector 16.

In one embodiment, telescopic column 108 includes any number, such as 2 or 4, of portions, such as portions 116, 118, and 120. In another embodiment, detector 16 is supported by a table instead of detector stand 102. In yet another embodiment, detector 14 is supported by a detector stand and a detector holder instead of being mechanically coupled to detector 16 via hinge 126.

Figure 3:
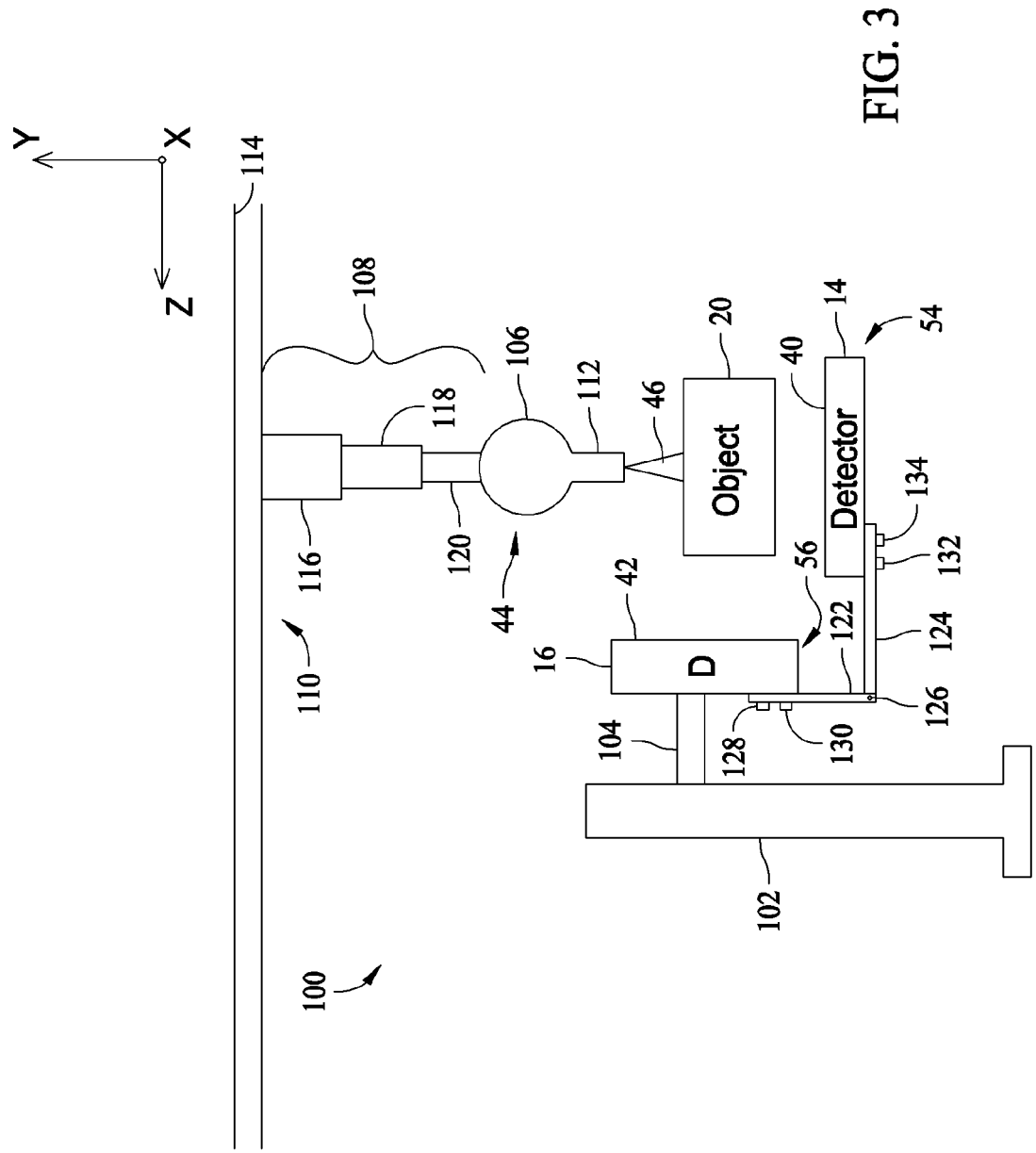
FIG. 3 is a side view of another embodiment of the system of FIG. 2.

FIG. 3 is a side view of another embodiment of system 100 for reducing movement of an object. Based on the acquisition parameters, system controller 30 controls source 106 via source driver system 24 to changes a position of source 106 from position 50 to position 44. When source 106 is at position 44, beam 46 is generated and an image of object 20 is generated by image processor 36 from the electrical signals generated by detector 14. Moreover, when source 106 is at position 44, an output of nozzle 112 from which beam 46 is output faces plane 40 of detector 14. In one embodiment, the image data acquired from position 44 is acquired before the image data is acquired from position 50.

Figure 4:
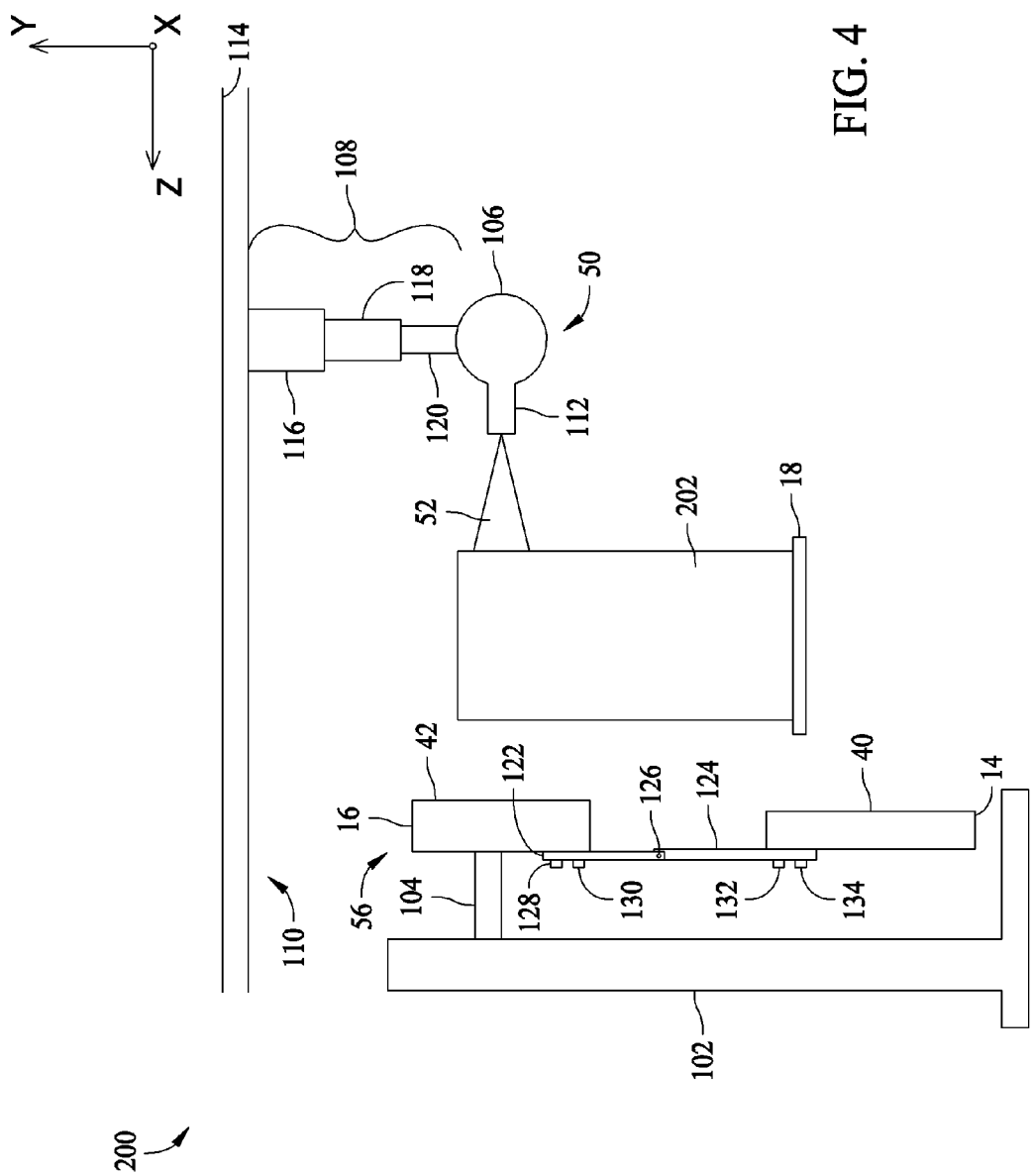
FIG. 4 is a side view of an embodiment of a system for reducing movement of an object.

FIG. 4 is a side view of an embodiment of a system 200 for reducing movement of an object. The user forms an angle of 180 degrees between planes 40 and 42 by changing, via hinge 126, an angle of support 122 with respect to support 124. An object 202 of the subject is placed on support 18 and a depth, parallel to the y-axis of object 202 extends parallel to plane 42, parallel to supports 122 and 124, and parallel to plane 40. A field-of-view of detector 16 does not encompass entire object 202. Similarly, a field-of-view of detector 14 does not encompass entire object 202. Examples of object 202 include a spine of the subject and a limb of the subject. Based on the acquisition parameters, system controller 30 controls source driver system 24 to position source 106 at position 50. When source 106 is at position 50, source 106 generates beam 52 that passes through an upper sub-portion of a side portion, such as a lateral side, of object 202. Detector 16 detects a portion of beam 52 output from object 202 to generate a plurality of electrical signals that are read by detector controller 38 and processed by image processor 36 to generate an image, such as an x-ray or a gamma ray image, of the upper sub-portion of object 202. As an example, image processor 36 applies FBP or alternatively MIP, to generate a computed tomography (CT) image of the upper sub-portion of object 202. Detector controller 38 reads the electrical signals from detector 16 to acquire image data when source 106 is at position 50.

Figure 5:
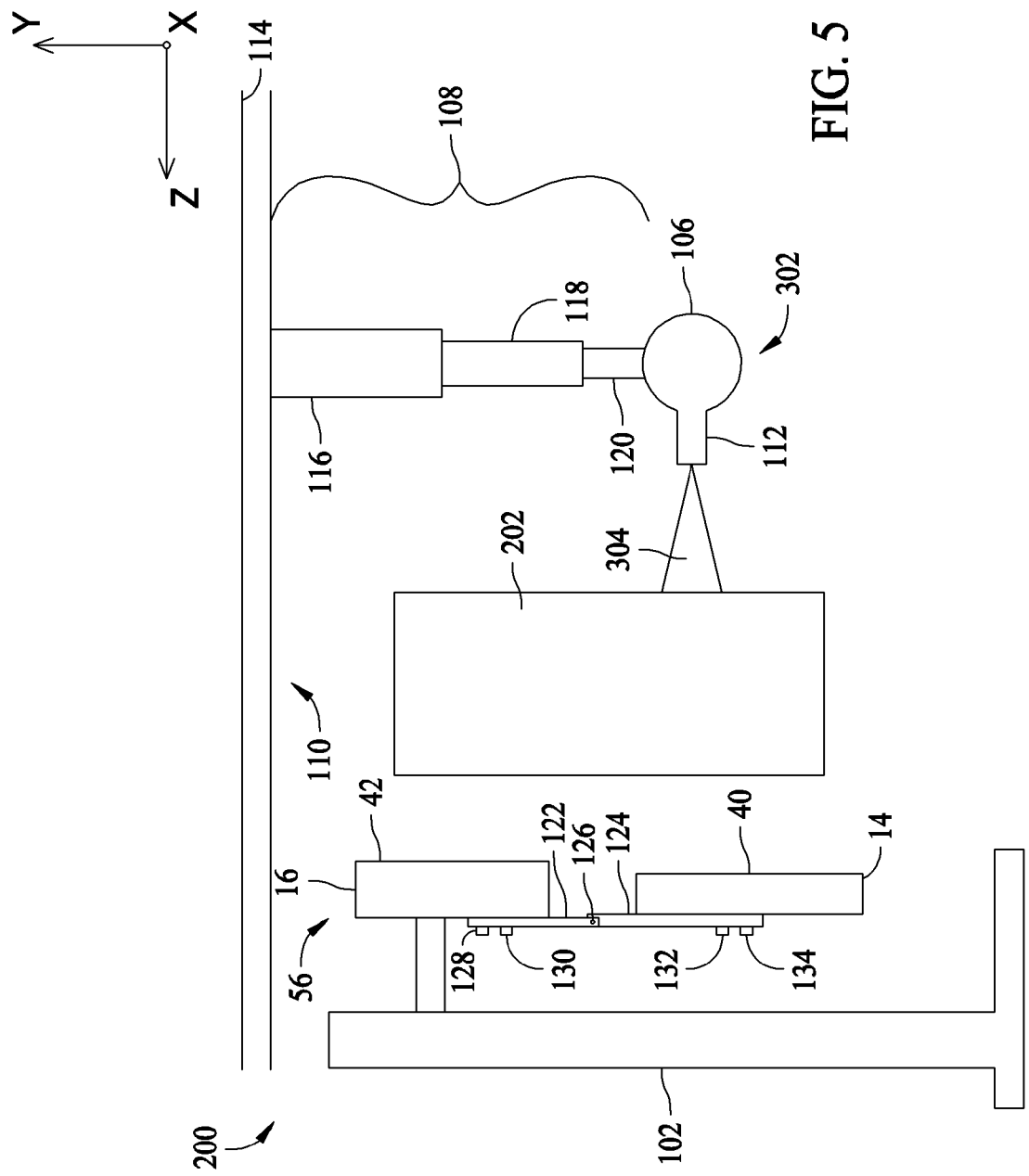
FIG. 5 is a side view of another embodiment of the system of FIG. 4.

FIG. 5 is a side view of another embodiment of system 200 for reducing movement of an object. Based on the acquisition parameters, system controller 30 controls source driver system 24 to drive source 106 from position 50 to a position 302. Moreover, based on the acquisition parameters, system controller 30 controls the power source within source driver system 24 to provide an amount of power to source 106 to activate source 106 for a pre-determined period of time. When source 106 is at position 302, source 106 generates a beam 304, such as an x-ray beam or a gamma ray beam, directed towards detector 14. Moreover, when source 106 is at position 302, output of nozzle 112 from which beam 304 is output faces detector 14. Beam 304 passes through a lower sub-portion of side portion of object 202 when source 106 is activated at position 302. The lower sub-portion is located at a lower position parallel to the y-axis than the upper sub-portion. Beam 304 passes through the lower sub-portion of object 202 to generate a portion detected by detector 14. When source 106 is at position 302, detector 14 receives the portion of beam 304 from object 202 to generate a plurality of electrical signals. Detector controller receives the electrical signals from detector 14 and the electrical signals are processed by image processor 36 to generate an image, such as an x-ray image or a gamma ray image, of the lower sub-portion of object 202. Detector controller 38 reads the electrical signals from detector 14 to acquire image data when source 106 is at position 302. It is noted that the acquisition parameters are not input by the user between an end of acquisition of the image data from detector 16 when source 106 is at position 50 and a beginning of the acquisition of image data from detector 14 when source 106 is at position 302.

In one embodiment, the image data from position 302 is acquired before the image data is acquired from position 50. In another embodiment, when source 106 is at position 50, source 106 generates beam 52 that passes through an upper sub-portion of a front portion, such as an anterior side, of object 202 and when source 106 is at position 302, source 106 generates beam 304 that passes through a lower sub-portion of the front portion of object 202. The lower sub-portion of the front portion of object 202 is lower, along the y-axis, than a location of the upper sub-portion of the front portion of object 202. In yet another embodiment, when source 106 is at position 50, source 106 generates beam 52 that passes through an upper sub-portion of a back portion, such as a posterior side, of object 202 and when source 106 is at position 302, source 106 generates beam 304 that passes through a lower sub-portion of the back portion of object 202. The lower sub-portion of the back portion of object 202 is lower, along the y-axis, than a location of the upper sub-portion of the back portion of object 202. In still another embodiment, image processor 36 combines, such as sums, the image data acquired when source 106 is at position 50 with the image data acquired when source 106 is at position 302 to generate combined image data that is processor by image processor 36 to generate an image, such as an x-ray image or a gamma ray image, of either side portion, the front portion, or the back portion of object 202. For example, image processor 36 sums the image data acquired when source 106 is at position 50 with the image data acquired when source 106 is at position, and reconstructs, such as by applying FBP or MIP, the combined image data to generate an image. In another embodiment, system controller 30 drives source 106 to position 302 to acquire image data from detector 14, drives source 106 from position 302 to position 50 to acquire image data from detector 16 and the user inputs, before an end of acquisition of the image data at position 302 and before a beginning of acquisition of image data at position 50, the acquisition parameters that dictate acquiring image data at position 302, that dictate driving source 106 from position 302 to position 50, and that dictate acquiring image data at position 50.

Figure 6:
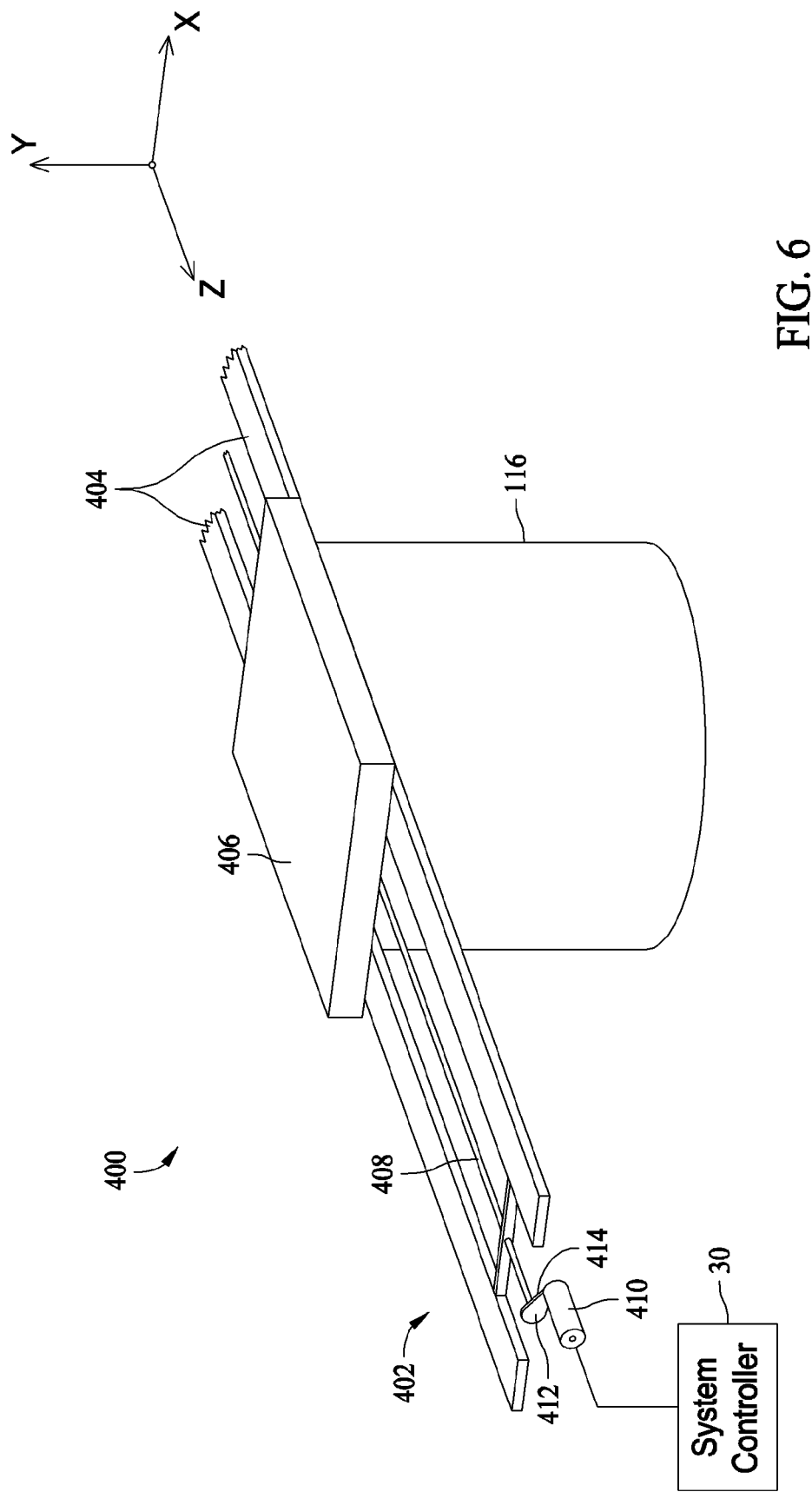
FIG. 6 is an isometric view of an embodiment of a system for reducing movement of an object.

FIG. 6 is an isometric view of an embodiment of a system 400 for reducing movement of an object. System 400 includes system controller 30 and a source driver system 402, which is an example of source driver system 24. Source driver system 402 includes a track 404 parallel to the z-axis, a translatable block 406, a rod 408 that is threaded and that passes through translatable block 406, a motor 410 including a stator and a rotor, a wheel 412 coupled via a belt 414 to motor 410, and portion 116 of telescopic column 108.

Based on the acquisition parameters, system controller 30 sends a system controller command signal to motor 410. Upon receiving the system controller command signal, the rotor of motor 410 rotates to rotate wheel 412 via belt 414. The rotation of wheel 412 translates translatable block 406, parallel to the z-axis, along tracks 404. Translatable block 406 is mechanically attached, such as glued, welded, or bolted, to portion 116 and translation of translatable block 406 translates portion 116 and telescopic column 108 along tracks 404 parallel to the z-axis. Translation of portion 116 is performed to move source 106 to position 50 and to move source 106 from position 50 to position 44. System controller 30 sends a system controller command signal, such as an off signal, to motor 410 to stop rotation of motor 410. When motor 410 stops rotating, portion 116 stops translation parallel to the z-axis. In one embodiment, translation of portion 116 is performed to move source 12 to position 44 and to move source 106 from position 44 to position 50.

Figure 7:
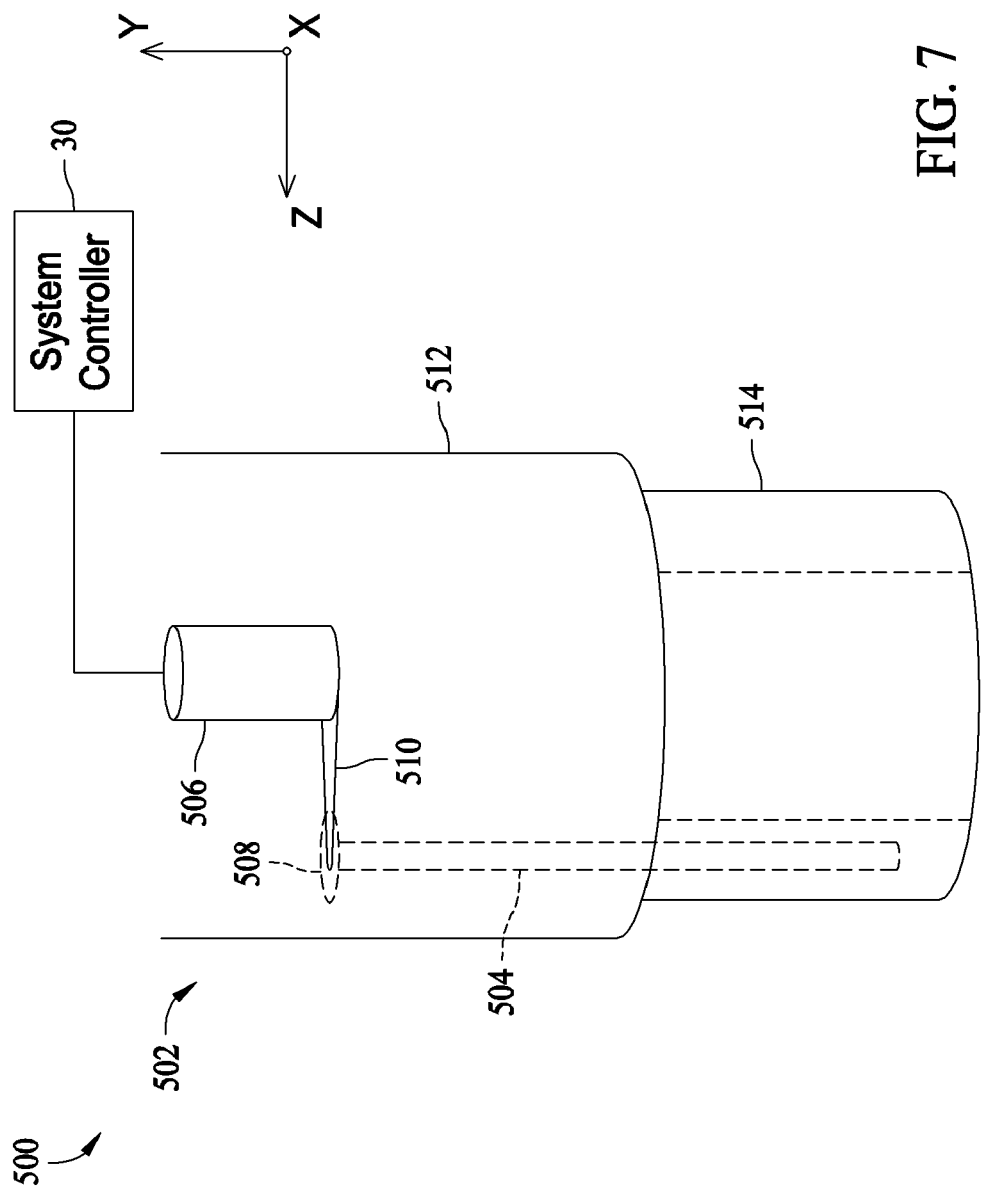
FIG. 7 is a view of an embodiment of a system for reducing movement of an object.

FIG. 7 is a view of an embodiment of a system 500 for reducing movement of an object. System 500 includes system controller 30 and a source driver system 502, which is an example of source driver system 24. Source driver system 502 includes a rod 504, a motor 506, a wheel 508, and a belt 510. System 500 includes a portion 512 of a telescopic column 513 and a portion 514 of telescopic column 513. Portion 512 is an example of portion 116 if portion 514 is an example of portion 118 and portion 512 is an example of portion 118 if portion 514 is an example of portion 120. Portion 512 is mechanically coupled to portion 514 via rod 504 that is threaded. Rod 504 is attached to wheel 508 that is mechanically connected to motor 506 via belt 510. Motor 506 includes a stator and a rotor. System controller 30 sends a system controller command signal to motor 510 to rotate the rotor of motor 510. The rotation of rotor of motor 510 rotates rod 504 and the rotation of rod 504 translates portion 514 with respect to portion 512 parallel to the y-axis. The translation of portion 514 with respect to portion 512 translates telescopic column 108 parallel to the y-axis to drive source 106 to position 50 and to drive source 106 from position 50 to position 44. When system controller 30 sends another system controller command signal to motor 506, the rotor of motor 506 stops rotating to stop translation of portion 514 with respect to portion 512 parallel to the y-axis.

In one embodiment, the translation of portion 514 with respect to portion 512 is performed when driving source 106 to position 44 at which image data from beam 46 is acquired and is performed when driving source 106 from position 44 to position 50 at which image data from beam 52 is acquired. In another embodiment, the translation of portion 514 with respect to portion 512 translates telescopic column 108 to drive source 106 to position 50 at which image data from beam 52 is acquired and to drive source 106 from position 50 to position 302 at which image data from beam 304 is acquired. In yet another embodiment, the translation of portion 514 with respect to portion 512 translates telescopic column 108 to drive source 106 to position 302 at which image data from beam 304 is acquired and to drive source 106 from position 302 to position 50 at which image data from beam 52 is acquired.

Figure 8:
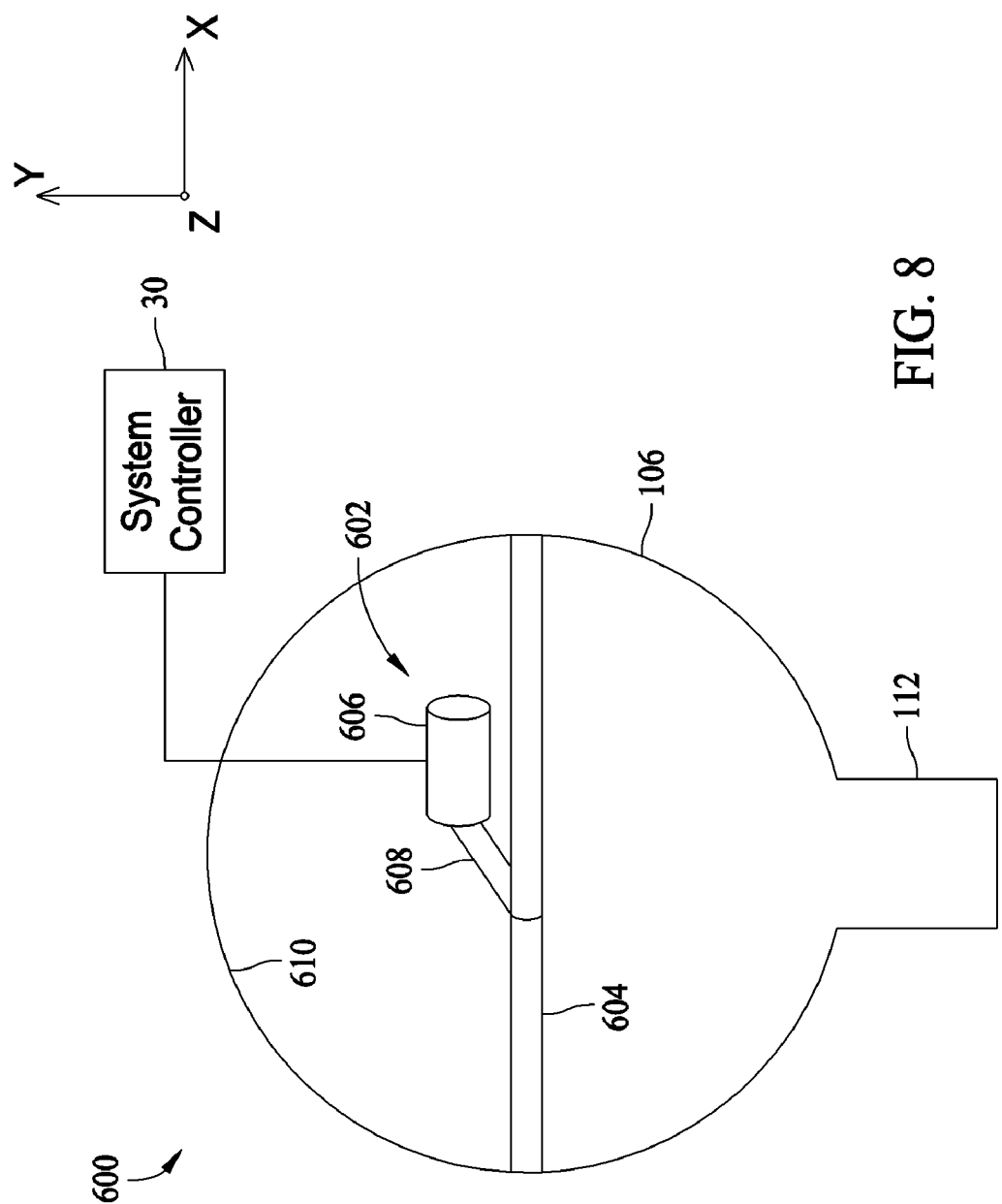
FIG. 8 is a view of an embodiment of a system for reducing movement of an object.

FIG. 8 is a view of an embodiment of a system 600 for reducing movement of an object. System 600 includes system controller 30, source 106, and a source driver system 602, which is an example of source driver system 24. Source driver system 602 includes a rod 604, a motor 606, and a belt 608. Motor 606 includes a rotor and a stator. System controller 30 sends a system controller command signal to motor 606 to rotate the rotor of motor 606. Rod 604 that is mechanically attached, such as glued or welded, to an inside surface 610 of source 106, rotates upon rotation of the rotor of motor 606. Source 106 rotates clockwise or alternatively counterclockwise with respect to and x-axis. The x-axis is perpendicular to the y and z axes and the y-axis is perpendicular to the z-axis. Rotation of source 106 is performed to drive source 106 to position 50 and to drive source 106 from position 50 to position 44. For example, rotation of source 106 is performed so that nozzle 112 faces plane 42 and further rotation of source 106 is performed so that nozzle 112 faces plane 40. When system controller 30 sends another system controller command signal, such as an off signal, to motor 606, the rotor of motor 606 stops rotation to stop source 106 to rotate with respect to the x-axis. In one embodiment, rotation of source 106 is performed to drive source 106 to position 44 at which image data is acquired from beam 46 and to drive source 106 from position 44 to position 50 at which image data is acquired from beam 52.

Figure 9:
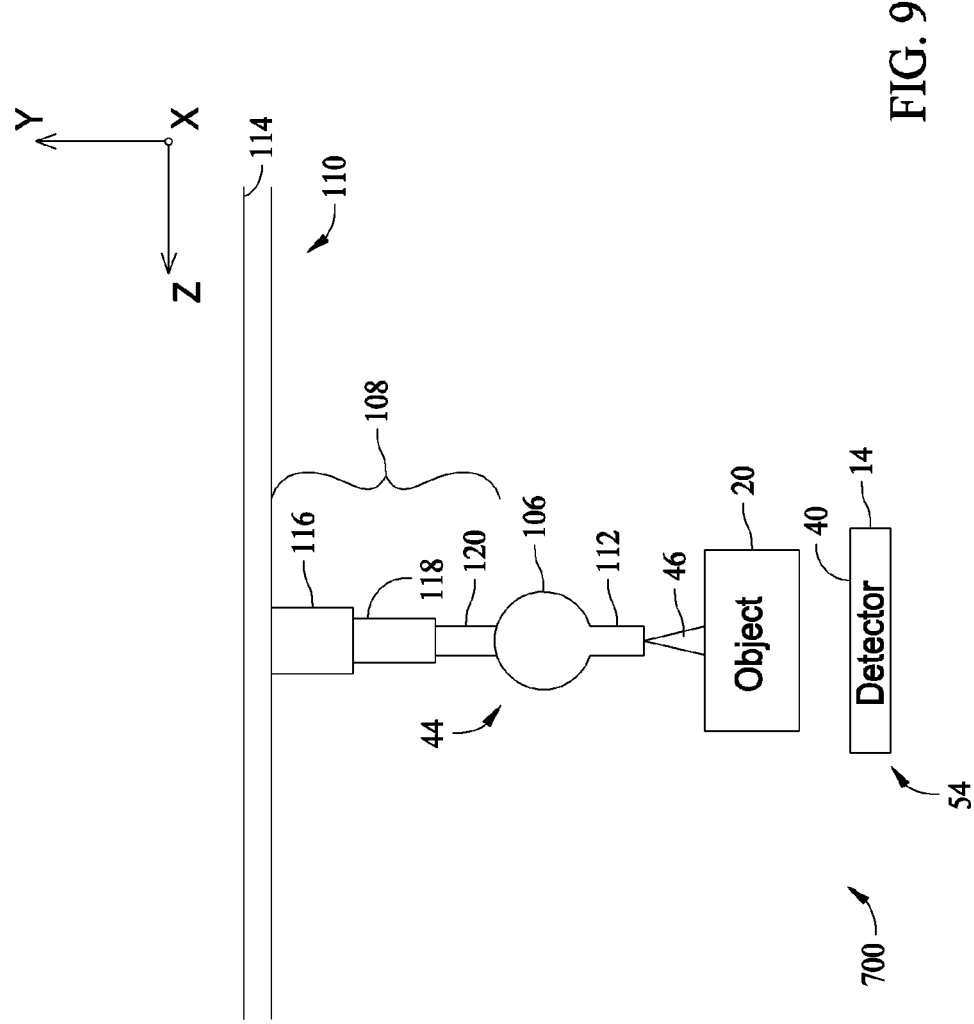
FIG. 9 is a side view of an embodiment of a system for reducing movement of an object.

FIG. 9 is a side view of an embodiment of a system 700 for reducing movement of an object. System 700 includes track system 110, telescopic column 108, source 106, and detector 14. Detector 14 detaches from detector 16. For example, detector 14 is not mechanically coupled to detector 14 via supports 122 and 124 and hinge 126. Based on the acquisition parameters, system controller 30 controls detector driver system 34 to drive detector 14 to position 54. When detector 14 is at position 54 and source 106 is at position 44, source 106 generates beam 46 that passes through the top portion of object 20 to generate the portion of beam 46 and detector 14 detects the portion of beam 46 to generate a plurality of electrical signals.

Figure 10:
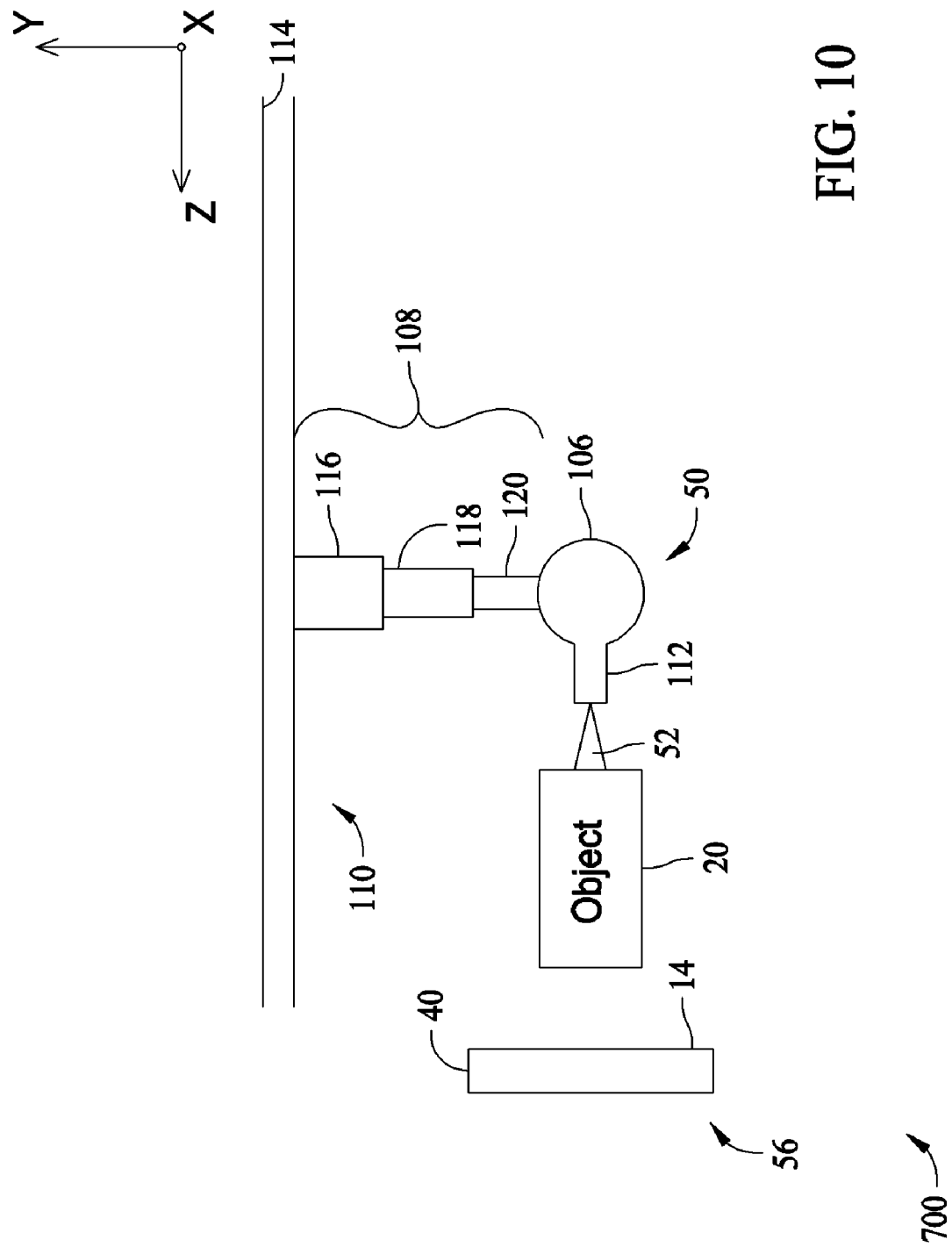
FIG. 10 is a side view of another embodiment of the system of FIG. 9.

FIG. 10 is a side view of another embodiment of system 700 for reducing movement of an object. System 700 includes telescopic column 108, source 106, and detector 14. Based on the acquisition parameters, system controller 30 controls detector driver system 34 to drive detector 14 from position 54 to position 56. When source 106 is at position 50 and detector 14 is at position 56, source 106 generates beam 52 that passes through the side portion of object 20 to generate the portion of beam 52 and detector 14 detects the portion of beam 52 to generate a plurality of electrical signals. It is noted that the acquisitions parameters are input by the user via input device 26 to system controller 30 before an end of the acquisition of the image data when source 106 is at position 44 and detector 14 is at position 54 and before a beginning of the acquisition of the image data when source 106 is at position 50 and detector 14 is at position 56. For example, system controller 30 does not receive the acquisition parameters from the user between an end of acquisition of the image data from detector 14 when source 12 is at position 44 and detector 14 at position 54 and a beginning of the acquisition of the image data from detector 16 when source 12 is at position 50 and detector 14 at position 56.

In one embodiment, based on the acquisition parameters, system controller 30 controls detector driver system 34 to drive detector 14 to position 56 at which image data is acquired from beam 52 and to drive detector 14 from position 56 to position 54 at which image data is acquired from beam 46. In the embodiment, system controller 30 does not receive the acquisition parameters from the user between an end of acquisition of the image data from detector 14 when source 12 is at position 50 and detector 14 at position 56 and a beginning of the acquisition of the image data from detector 16 when source 12 is at position 44 and detector 14 at position 54. In another embodiment, when source 106 is at position 50 and detector 14 is at position 56, source 106 generates beam 52 that passes through the top portion of object 20 to generate the portion of beam 52 and when source 106 is at position 44 and detector 14 is at position 54, source 106 generates beam 46 that passes through the side portion of object 20.

Figure 11:
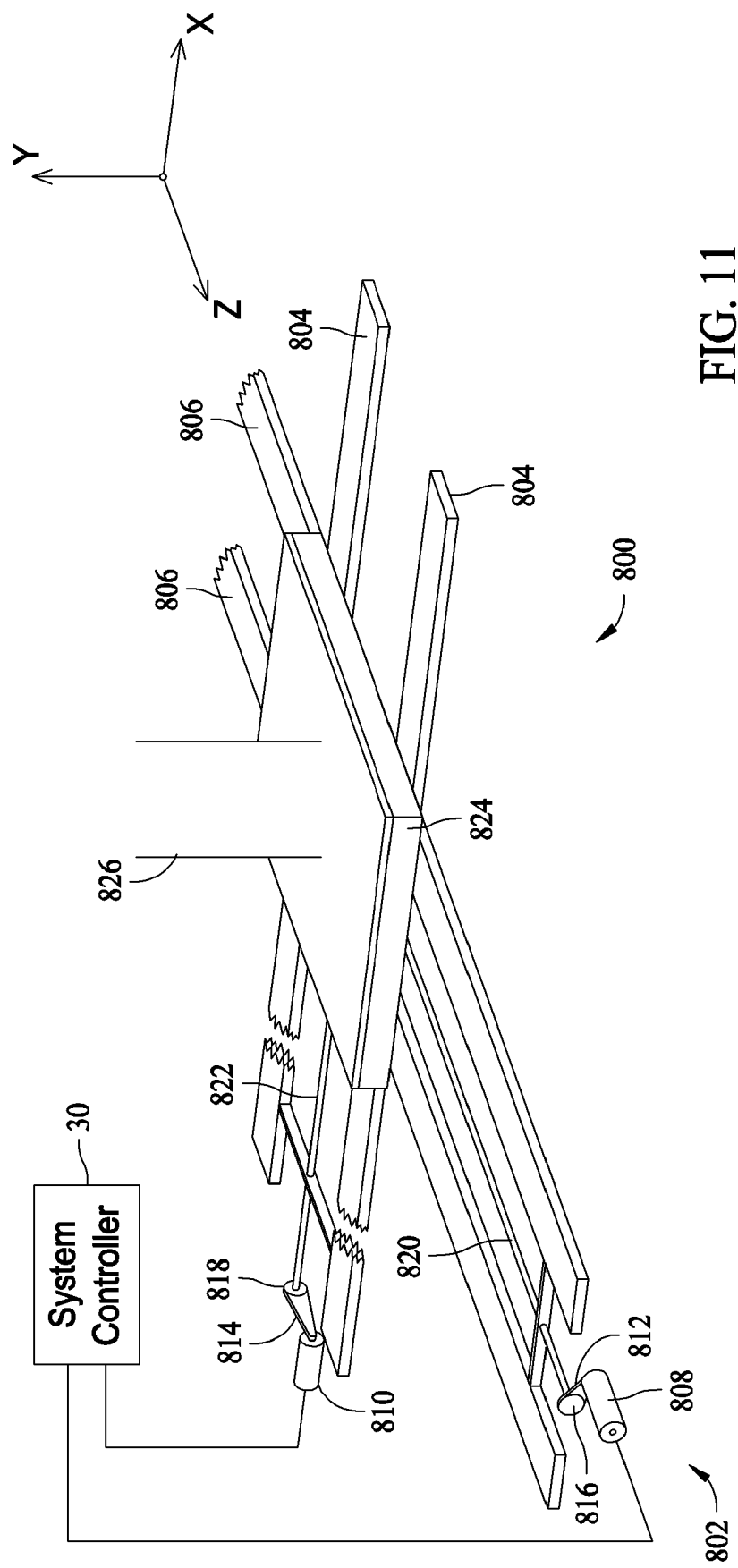
FIG. 11 is an isometric view of an embodiment of a system for reducing movement of an object.

FIG. 11 is an isometric view of an embodiment of a system 800 for reducing movement of an object. System 800 includes system controller 30 and a detector driver system 802, which is an example of detector driver system 34. Detector driver system 802 includes a plurality of tracks 804 and 806, a plurality of motors 808 and 810, a plurality of belts 812 and 814, a plurality of wheels 816 and 818, a detector stand 826 that supports detector 14, a plurality of rods 820 and 822 that are threaded, and a translatable block 824. Translatable block 824 is attached, such as bolted or glued, to detector stand 826 that is mechanically coupled to detector 14. Each motor 808 and 810 includes a rotor and stator. Based on the acquisition parameters, system controller 30 senses a system controller command signal to motor 808. The rotor of motor 808 rotates upon receiving the system controller command signal. Rod 820 rotates upon rotation of the rotor of motor 808 and translatable block 824 translates, parallel to the z-axis, upon rotation of rod 820.

Moreover, system controller 30 sends a system controller command signal to motor 810. The rotor of motor 810 rotates upon receiving the system controller command signal from system controller 30. Rod 822 rotates upon rotation of the rotor of motor 810 and translatable block 824 translates, parallel to the x-axis, upon rotation of rod 822. Translatable block 824 translates parallel to the x-axis and the z-axis to drive detector 14 to position 54 and from position 54 to position 56. When system controller 30 sends a system controller command signal, such as an off signal, to motor 808, the rotor of motor 808 stops rotation to stop translatable block from translating parallel to the z-axis. Moreover, when system controller 30 sends a system controller command signal, such as an off signal, to motor 810, the rotor of motor 810 stops rotation to stop translatable block from translating parallel to the x-axis. In one embodiment, system controller 30 controls motors 808 and 810 to translate translatable block 824 in an xz plane, formed between the x and z axes, to drive detector 14 to position 56 at which image data from beam 52 is acquired and to drive detector 14 from position 56 to position 54 at which image data from beam 46 is acquired.

Figure 12:
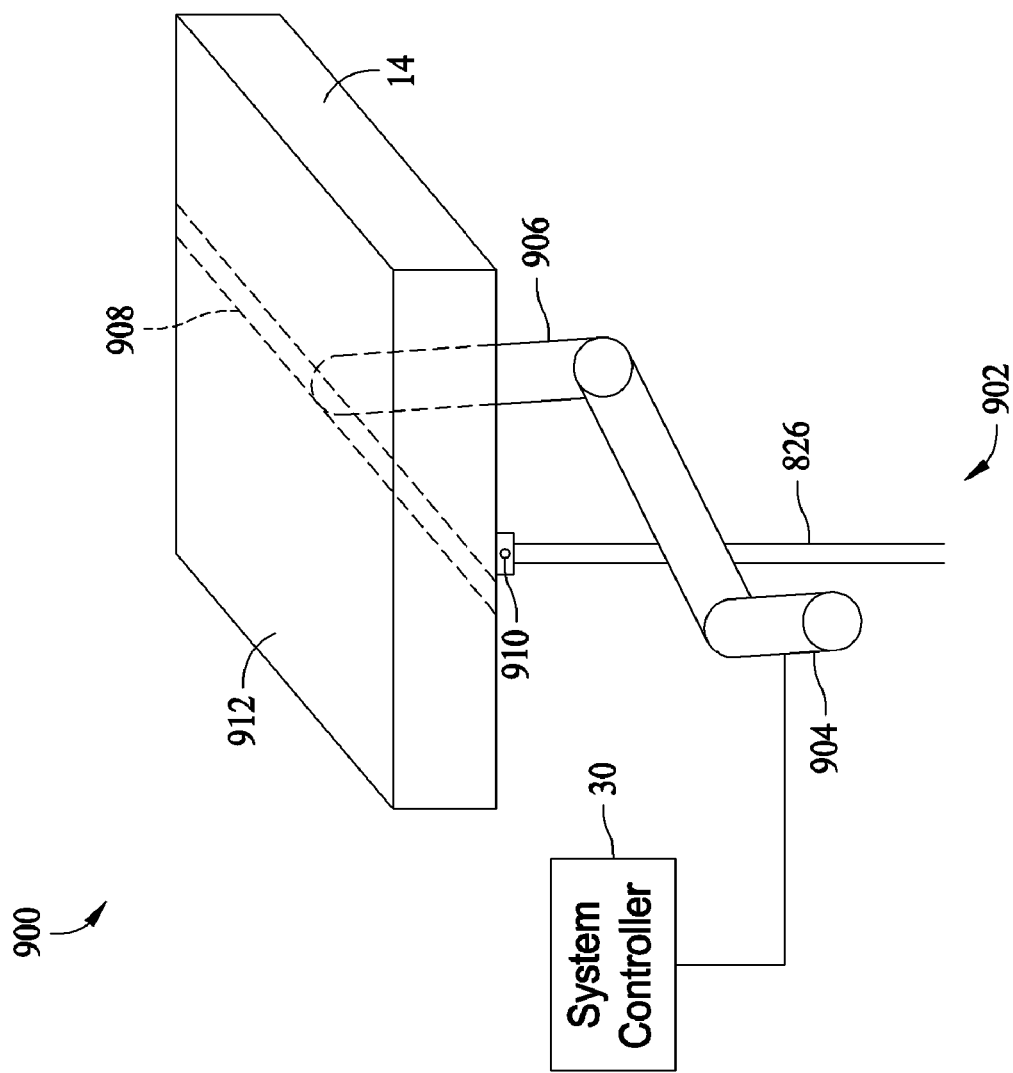
FIG. 12 is an isometric view of an embodiment of a system for reducing movement of an object.

FIG. 12 is an isometric view of an embodiment of a system 900 for reducing movement of an object. System 900 includes system controller 30 and a detector driver system 902. Detector driver system 902 is an example of detector driver system 34. Detector driver system 902 includes a motor 904, a belt 906, a rod 908, and a hinge 910. Rod 908 is mechanically attached, such as glued or welded, to a plurality of inside surfaces of a housing 912 of detector 14. Motor 904 includes a rotor and a stator. Detector 14 hinges with respect to detector stand 826 via hinge 910. System controller 30 sends a system controller command signal to motor 904. Upon receiving the system controller command signal, the rotor of motor 904 rotates either clockwise or counterclockwise with respect o the x-axis. Upon rotation of the rotor of motor 904, rod 908, which is connected via belt 906 to the rotor, rotates to rotate housing 912 either clockwise or counterclockwise with respect to the x-axis.

System controller 30 controls motor 904 to rotate detector 14 to bring detector 14 to position 54 and to change detector 14 from position 54 to position 56. System controller 30 sends another system controller command signal, such as an off signal, to motor 904 to stop the rotor of motor 904 from rotating. When the rotor of motor 904 stops rotating, detector 14 stops rotation with respect to the x-axis. In one embodiment, system controller 30 controls motor 904 to rotate detector 14 to change detector 14 to position 56 at which image data from beam 52 is acquired and to change detector 14 from position 56 to position 54 at which image data from beam 46 is acquired.

Figure 13:
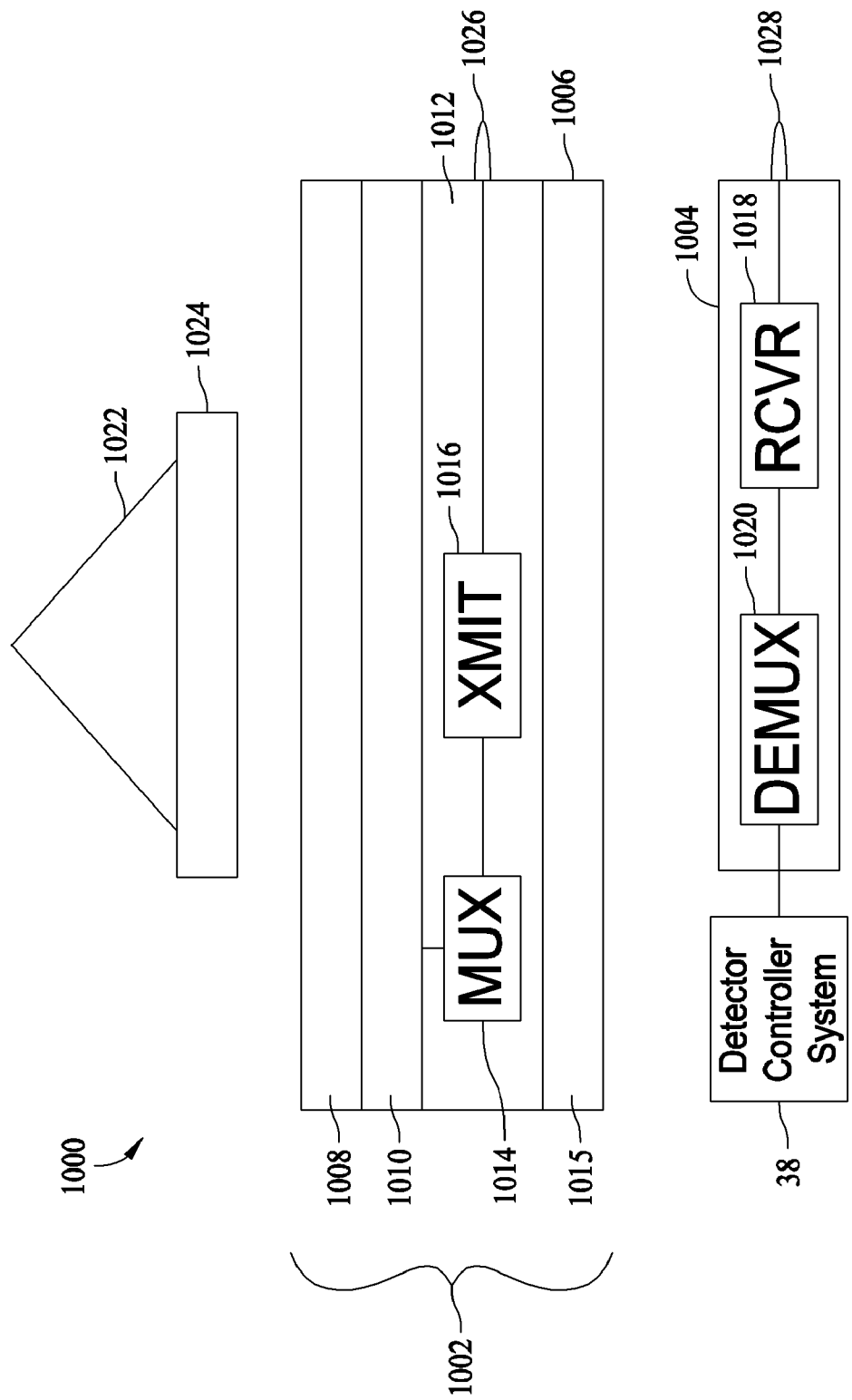
FIG. 13 is a block diagram of an embodiment of a system for reducing movement of an object.

FIG. 13 is a block diagram of an embodiment of a system 1000 for reducing movement of an object. System 1000 includes a detector 1002 and a receiver section 1004. Detector 1002 is an example of any of detectors 14 and 16. Detector 1004 includes a housing 1006, a scintillator layer 1008 made of a scintillator, a photodiode array layer 1010 made of an array of photodiodes, a transmitter section 1012, and a substrate 1014 supporting scintillator layer 1008, photodiode array 1010, and transmitter section 1012. Transmitter section 1012 includes a multiplexer 1015 and a transmitter 1016. Receiver section 1004 includes a receiver 1018 and a demultiplexer 1020 that electrically couples to detector controller 38. Scintillator array 1008 receives a portion of beam 1022, which is an example of any of beams 46, 304, and 52, and converts the portion into visible light. The portion of beam 1022 is received by scintillator array 1008 after beam 1022 passes through an object 1024, which is an example of any of objects 20 and 202. Photodiode array 1010 receives the visible light from scintillator array 1008 to generate a plurality of electrical signals. Multiplexer 1015 multiplexes the electrical signals received from photodiode array 1010 to generate a multiplexer output signal. Transmitter 1016 may amplify the multiplexer output signal and modulates the multiplexer output signal onto a carrier frequency to generate a transmitter output signal, such as a radiofrequency signal that is transmitted via an antenna 1026.

An antennal 1028 electrically coupled to receiver 1018 receives transmitter output signal. Receiver 1018 may change a magnitude of the transmitter output signal and demodulates the transmitter output signal to generate a receiver output signal. Demultiplexer 1020 demultiplexes the receiver output signal to generate a plurality of demultiplexed output signals that are read by detector controller 38. Detector controller 38 reads the demultiplexed output signals to acquire image data from beam 1022. In an embodiment, any of detectors 14 and 16 can be electrically coupled to a docking station.

Technical effects of the herein described systems and methods for reducing movement of an object 20 include reducing, such as eliminating, movement of the subject by providing detector 14, in the room, in addition to detector 16. Moreover, a movement of the subject is reduced because an input of the acquisition parameters is not needed between an end of the acquisition of the image data from detector 16 at position 56 and a beginning of the acquisition of image data from detector 14 at position 54. Additionally, movement of the subject is reduced because inputting the acquisition parameters is not needed between the end of the acquisition of image data from detector 16 at position 56 and the beginning of the acquisition of the image data from detector 14 at position 54. The subject does not need to move to obtain different views of either object 20 or object 202. Moreover, source 106 and any of detectors 14 and 16 do not need to be manually moved to image different views of either object 20 or object 202. Additionally, the acquisition parameters are not entered via input device 26 into system controller 30 between an exposure of object 20 to beam 46 and an exposure of object 20 to beam 52. Moreover, the acquisition parameters are not entered via input device 26 into system controller 30 between an exposure of object 202 to beam 52 and an exposure of object 202 to beam 304.

Furthermore, the subject does not need to be moved, such as from either a supine or a prone position to a lateral position, or alternatively from the lateral position to either the spine or the prone position, to image view of the subject. For example, object 20 does not need to be moved between the acquisition of image data from beam 46 and the acquisition of image data from beam 52. As another example, object 20 does not need to be moved between the acquisition of image data from beam 52 and the acquisition of image data from beam 302. As a result, a time of imaging either object 20 or object 202 is reduced. The subject may be unable to move in the emergency room.

While the invention has been described in terms of various specific embodiments, those skilled in the art will recognize that the invention can be practiced with modification within the spirit and scope of the claims.

What is claimed is:

1. A system for reducing movement of an object, said system comprising:
   a first detector configured to detect a first beam and generate a first image data therefrom; and
   a second detector configured to detect a second beam and generate a second image data therefrom, wherein the first and second detectors are located within a radiography room.

2. A system in accordance with claim 1, wherein the first detector is mechanically attached to the second detector.

3. A system in accordance with claim 1, wherein the first detector is mechanically attached to the second detector via a hinge.

4. A system in accordance with claim 1 further comprising:
   a source configured to generate the first and second beams;
   a source driver system;

a system controller configured to receive a plurality of acquisition parameters, wherein said system controller is configured to command said source driver system to drive said source from a first position to a second position based on the acquisition parameters.

5. A system in accordance with claim 1 further comprising:
a source configured to generate the first and second beams;
a source driver system;
a system controller configured to receive a plurality of acquisition parameters, wherein said system controller is configured to command said source driver system to drive said source from a first position to a second position based on the acquisition parameters, wherein at the first position, an output of said source that outputs the first beam faces said first detector, and wherein at the second position, an output of said source that outputs the second beam faces said second detector.

6. A system in accordance with claim 1, wherein said first detector has a first plane and said second detector has a second plane, and an angle formed between said first and second planes ranges from ninety degrees to one-hundred and eighty degrees.

7. A system in accordance with claim 1, wherein said first and second detectors are located within an emergency room of a medical facility.

8. A system for reducing movement of an object, said system comprising:
a source configured to generate a first beam and a second beam;
a detector configured to detect the first beam at a first position of said detector beam and generate a first image data therefrom, wherein said detector is configured to detect the second beam at a second position of said detector beam and generate a second image data therefrom, wherein the first position is other than the second position.

9. A system in accordance with claim 8 further comprising:
a detector driver system; and
a system controller configured to control said detector driver system to drive said detector from the first position to the second position.

10. A system in accordance with claim 8 further comprising a detector controller electrically coupled to said detector, wherein said detector controller is configured to read a first set of image data representing a first portion of the object when said detector is at the first position, and said detector controller is configured to read a second set of image data representing a second portion of the object when said detector is at the second position, wherein the first portion is other than the second portion.

11. A system in accordance with claim 8 further comprising a detector controller electrically coupled to said detector, wherein said detector controller is configured to read a first set of image data representing a first portion of the object when said detector is at the first position, and said detector controller is configured to read a second set of image data representing a second portion of the object when said detector is at the second position, wherein the first portion is other than the second portion, wherein the first set of image data represents one of a posterior and an anterior side and the second set of image data represents a lateral side of the object.

12. A system in accordance with claim 8, wherein said source is at a third position when said detector is at the first position and said source is at a fourth position when said detector is at the second position, wherein the third position is other than the fourth position.

13. A system in accordance with claim 8, wherein said source is at a third position when said detector is at the first position and said source is at a fourth position when said detector is at the second position, wherein the third position is other than the fourth position, said system further comprising a system controller configured to receive a plurality of acquisition parameters representing the first, second, third, and fourth positions before said detector moves from the first position to the second position and said source moves from the third position to the fourth position.

14. An imaging system comprising:
a first detector configured to detect a first beam and generate a first image data therefrom;
a second detector configured to detect a second beam and generate a second image data therefrom, wherein the first and second detectors are located within a radiography room; and
an image processor configured to generate a first image and a second image from the first and second image data acquired from at least one of a portion of the first beam and a portion of the second beam.

15. A system in accordance with claim 14, wherein the first detector is mechanically attached to the second detector.

16. A system in accordance with claim 14, wherein the first detector is mechanically attached to the second detector via a hinge.

17. A system in accordance with claim 14 further comprising:
a source configured to generate the first and second beams;
a source driver system;
a system controller configured to receive a plurality of acquisition parameters, wherein said system controller is configured to command said source driver system to drive said source from a first position to a second position based on the acquisition parameters.

18. A system in accordance with claim 14 further comprising:
a source configured to generate the first and second beams;
a source driver system;
a system controller configured to receive a plurality of acquisition parameters, wherein said system controller is configured to command said source driver system to drive said source from a first position to a second position based on the acquisition parameters, wherein at the first position, an output of said source that outputs the first beam faces said first detector, and wherein at the second position, an output of said source that outputs the second beam faces said second detector.

19. A system in accordance with claim 14, wherein said first detector has a first plane and said second detector has a second plane, and an angle formed between said first and second planes ranges from ninety degrees to one-hundred and eighty degrees.

20. A system in accordance with claim 14, wherein said first and second detectors are located within an emergency room of a medical facility.

* * * * *